United States Patent [19]
Henkel

[11] Patent Number: 5,531,123
[45] Date of Patent: Jul. 2, 1996

[54] REMOTE AND POWERLESS MINIATURE FATIGUE MONITOR AND METHOD

[76] Inventor: Daniel P. Henkel, 3 Curson Ct., Poquoson, Va. 23662

[21] Appl. No.: 334,680

[22] Filed: Nov. 4, 1994

[51] Int. Cl.$^6$ .................................................... G01N 3/00
[52] U.S. Cl. .............................. 73/795; 73/762; 73/799; 73/849; 73/786
[58] Field of Search .......................... 73/762, 775, 776, 73/799, 812, 849, 786, 795

[56] References Cited

U.S. PATENT DOCUMENTS

| | | | |
|---|---|---|---|
| 2,294,897 | 9/1942 | Ellis | 73/762 |
| 2,724,964 | 11/1955 | Singdale | 73/762 |
| 2,924,094 | 2/1960 | Hast | 73/88 |
| 3,765,230 | 10/1973 | Bohm et al. | 73/88 R |
| 3,774,443 | 11/1973 | Green et al. | 73/67.3 |
| 3,779,071 | 12/1973 | Thomas, Jr. et al. | 73/88.5 R |
| 3,786,679 | 1/1974 | Crites | 73/88.5 R |
| 3,789,657 | 2/1974 | Ching, Jr. et al. | 73/762 |
| 3,979,949 | 9/1976 | Smith | 73/88 R |
| 4,107,980 | 8/1978 | Crane et al. | 73/88 R |
| 4,255,049 | 3/1981 | Sahm et al. | 73/762 X |
| 4,255,974 | 3/1981 | Dufrane et al. | 73/776 |
| 4,292,851 | 10/1981 | Brewer | 73/762 |
| 4,546,652 | 10/1985 | Virkar et al. | 73/776 |
| 4,590,804 | 5/1986 | Brull | 73/762 |
| 5,022,275 | 6/1991 | Satoh et al. | 73/862.36 |
| 5,105,667 | 4/1992 | Satoh et al. | 73/862.36 |
| 5,227,731 | 7/1993 | Prabhakaran et al. | 324/718 |
| 5,237,875 | 8/1993 | de la Veaux | 73/775 |
| 5,325,721 | 7/1994 | Pendergrass, Jr. | 73/762 |
| 5,425,274 | 6/1995 | Creamer | 73/762 |

Primary Examiner—Richard Chilcot
Assistant Examiner—Elizabeth L. Dougherty
Attorney, Agent, or Firm—Raymond L. Greene

[57] ABSTRACT

A method and passive monitor for measurement of fatigue is provided. The method includes locating regions of high stress on a structure or material to be monitored, identifying the direction of principal stresses, and then aligning and bonding a specially fabricated passive fatigue monitor to the structure. After the structure has been subjected to a stress cycle, the passive fatigue monitor is removed and the striations formed in the monitor are evaluated. If necessary, contrast enhancement of striations can be performed prior to striation evaluation. Data from evaluations is assessed using rain flow cycle counting and Miners cumulative damage algorithms. The passive fatigue monitor is a small coupon of material fabricated from aluminum or other material known to form well-defined striations. The monitor is specially modified to contain a precrack which provides the location for striation formation.

18 Claims, 6 Drawing Sheets

REMOTE AND POWERLESS MINIATURE FATIGUE MONITOR AND METHOD

FIELD OF THE INVENTION

The invention relates to the field of fatigue testing and more particularly to fatigue testing using unpowered fatigue monitors.

BACKGROUND OF THE INVENTION

Prior art fatigue monitors and passive fatigue monitors may be classified into four general methods. Visual crack length methods are the most numerous. Examples include Crane (U.S. Pat. No. 4,107,980), Smith (U.S. Pat. No. 3,979,949), Crites (U.S. Pat. No. 3,786,679), Brull (U.S. Pat. No. 4,590,804), and de la Veaux (U.S. Pat. No. 5,237,875). Change in electrical resistance methods include: Duframe (U.S. Pat. No. 4,255,974), Bohm (U.S. Pat. No. 3,765,230) and Prabhakaran (U.S. Pat. No. 5,227,731). Acoustic monitoring is illustrated in Green (U.S. Pat. No. 3,774,443) and (U.S. Pat. No. 4,265,120). Magnetic monitoring, the fourth method, was described by Satoh (U.S. Pat. No. 5,022,275 and U.S. Pat. No. 5,105,667). As noted by de la Veaux, the Brull invention (U.S. Pat. No. 4,590,804) has limited applications since the mounting techniques are improper and it is not adaptable for remote monitoring. He, therefore, patented improvements in the form of ASTM test standards for adhesives that provide superior bonding and he indicates wire attachments that could be monitored to detect changes in conductivity.

There are certain limitations in the prior art. An examination of the de la Veaux and Brull patents is illustrative of these limitations. As an example, the Brull patent, in FIG. 3, describes the cycles to failure as a function of stress amplitude. At a stress amplitude of 13 ksi, the plot predicts failure within 160,000 cycles for coupon 20 or 340,000 for coupon 14. Specific results from test on 7075 aluminum beam are presented in the table (Col. 7, 57–63) describing the cycles for failure to be 163,600 for coupon 20 and 286,700 for coupon 14. He also claims that the structural member being monitored failed at 486,000 cycles. Therefore, the claim is that a failure in coupon 14 represents 33% of service life and a failure in coupon 20 represents approximately 60%.

Both inventions assume that the "fatigue fuse" is placed on a new structure. Otherwise, the fuse does not represent an accurate percentage of service life when they fail. For example, if a fuse was placed on the above structural member that had already undergone 243,000 cycles, then the coupon 14 indication would be 67% instead of 33%. The structure would also have failed long before any indication by coupon 20. This situation illustrates major limitations of the Tensiodyne fatigue fuses. These limitations include the characteristic that fatigue monitoring applications are suitable only for existing structures and that fuses have no means of correction for prior stress history.

The fuse must be made from the same composition material as the structure being monitored for it to perform accurately. If the structure is coated, the fuse must have the same coating. This makes selection and use difficult since extra coating material must be kept on hand and material specifications for the structure must be available.

An additional limitation is that the de la Veaux patent claims to provide indication of three percentages of service life (Col. 7, 65–68) with no continuous or intermittent levels. If true monitoring is necessary, three data points would be insufficient over a structural loading period of many years. Also, the 75% maximum service life indication may not be sufficient on a 25 or 50 year structure. The remaining 25% (6 to 12 years) would not be monitored since all of the fuses would have already "blown".

Stress amplitudes vary considerably from one direction to another on a structure's surface and the previous inventions do not take this into consideration. The inventors apparently assume that the user will know to align the fuse with the principal (maximum) stresses in the structure since no method is described for doing so. If the cracks in the fuse are not perpendicular to the principal stresses, their propagation rates do not reflect the true damage in the structure and the fuse does not accurately monitor fatigue life.

Finally, the mechanical behavior of the test beam that was used by Brull as the basis for determining total service life and, therefore, the percentages predicted by the fuse elements, do not correspond to industry-accepted fatigue criterion for 7075 aluminum. An unnotched beam would require over 30 ksi to fail within 500,000 cycles, not 13 ksi. If the stress amplitude was 13 ksi, it would require over one trillion cycles to fail which is beyond any conceivable service life. Therefore, it is obvious that the test beam must have been notched and the total service life is highly dependent on the configuration of the notch. For instance, a 0.25 mm root radius notch in the test beam would reduce the service life from one trillion cycles at 14 ksi to approximately one million (the actual range is 1 to 10 million). A more acute notch may have dropped the cycles to the claim of 486,000 but, it can be seen that the accuracy of the fuse is very specific to the geometry of the fuse structure. If a range of 0.5 to 10 million cycles to failure is assumed, depending on the presence and shape of a notch, the percentage of life predicted by coupon 20 varies from 33% to 1.6%. The limitation imposed by this range of variance means that the fuse may only be used when the geometry of the structure is known and its fatigue behavior at the point of attachment has been characterized. As a result, fatigue fuses cannot be put into general use as the costly analysis required of each structural member, precludes economic use.

SUMMARY OF THE INVENTION

Accordingly, it is an object of the invention to provide a means and method for stress monitoring which includes correction for prior stress history.

It is another object of the invention to provide a stress monitor which may be used with structural materials different from the material of the monitor.

It is yet another object of the invention to provide a stress monitor which can be used with both coated and uncoated materials.

It is a further object of the invention to provide a stress monitor having a fixed geometry or physical configuration which is suitable for testing a variety of different structures.

It is still another object of the invention to provide a fatigue data storage technique based on microstructural changes that involve no electrical, acoustic, or magnetic signal monitoring.

Accordingly, a remote, powerless miniature fatigue monitor and method are provided. The fatigue monitor comprises a coupon fabricated from a metal having a face-centered cubic crystal structure or other material having well defined striation characteristics. Among the suitable metals are copper, nickel and aluminum. Among the suitable non-metallic materials are rubber, ceramic and polymer materials. Aluminum is used in the preferred embodiment because of its inherent corrosion-resistance, low density, machinability, and availability. The associated method includes attaching and stressing the fatigue monitor, removal of the monitor, striation enhancement and examination, and fatigue cycle projection.

BRIEF DESCRIPTION OF THE DRAWINGS

The foregoing objects and other advantages of the present invention will be more fully understood from the following detailed description and reference to the appended drawings wherein.

DETAILED DESCRIPTION OF THE INVENTION

Figure 1:
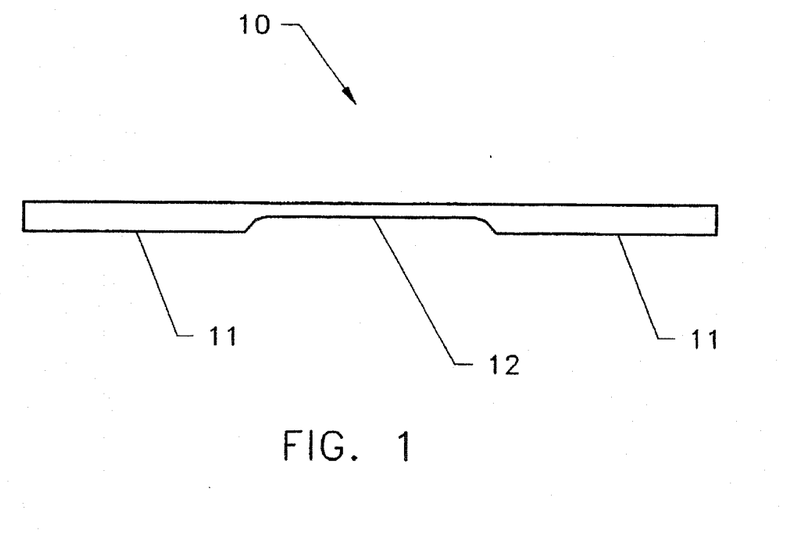
FIG. 1 is a side view of the passive fatigue monitor.

Referring now to FIG. 1, the passive fatigue monitor of the present invention, depicted generally by the reference numeral 10 is shown with its major structural features. Passive fatigue monitor 10 has bonding surfaces 11 along the lower surface of the monitor coupon. These bonding surfaces are separated by a machined section 12 which has been thinned to provide a plastic region of accelerated, fatigue-induced, striation formation. As may be further seen in FIG. 2, section 12 has a precrack 21. This precrack may be formed by sawing, notching or otherwise cutting the surface.

Figure 2:
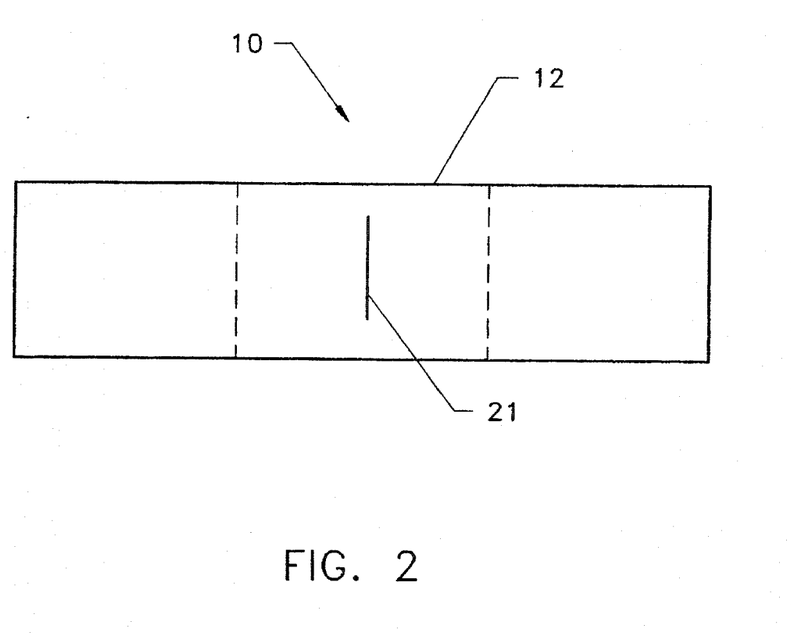
FIG. 2 is a top view of the passive fatigue monitor.

The passive fatigue monitor 10 is fabricated from materials having natural corrosion resistance so that the coupon need not be enclosed nor coated. In the metal embodiment, monitor 10 is fabricated using metals having face-centered cubic crystal structures. These metals form well-defined striations on {111} slip planes parallel to <110> slip directions. Among suitable metals are aluminum, copper and nickel. Alloys are also suitable, as are other materials such as ceramics, polymers, and rubber. In the preferred embodiment, aluminum is used to fabricate the monitor coupon. Further, the monitor, as depicted in FIGS. 1 and 2, adapts very well to surface mounting on aircraft or other vehicles where a low profile mounting is required. The monitor shown in FIG. 2 is approximately one-inch in length and provides only a slight protrusion from the surface to be tested.

The passive fatigue monitor design is one piece construction eliminating the need for costly assembly. The operational method described herein is dependent on the presence of a precrack which advances the fracture surface in incremental distances proportional to the applied cyclic stress. The boundaries of the crack advance are the striation peaks which become a permanent part of the fracture surface with each loading cycle. As shown in FIG. 1, the device has a small attachment surface 11 that permits adhesive bonding in a configuration that directly transfers the cyclic surface stresses of the structure to the precrack 21. While the striation spacing is proportional to the applied stress range, $\Delta\sigma$, it is more precisely defined as a function of the stress intensity range factor, $\Delta K$. This factor takes into account the two additional factors of crack length, a, and geometrical configuration, Y. The general relations are given by $$\Delta K = Y \cdot \Delta\sigma \sqrt{a}$$

and $$\text{striation spacing} \approx 6\, (\Delta K/E)^2$$

The specific relationship is determined by the geometric configuration and precrack length of the passive fatigue monitor design. These factors are the most critical part of the design since an accurate and precise interpretation of the striation data depends on a thorough understanding of the stress intensity at the crack tip.

Since striations are most clearly resolved at intermediate stress intensity levels, becoming difficult to observe at both the upper and lower thresholds, the geometrical configuration and precrack size of the passive fatigue monitor must be designed to operate in this regime. The device is configured for plane strain conditions, although the thickness is kept to a minimum. The reduced size of the plastic region 12 effectively concentrates the applied stresses at the precrack 21 thereby producing well-defined striations while being less sensitive to microstructural variations. A low profile is maintained such that the monitor is unobtrusive and does not interfere with the performance of the measured surface. Overall size in any dimension does not exceed 25 mm.

Figure 3:
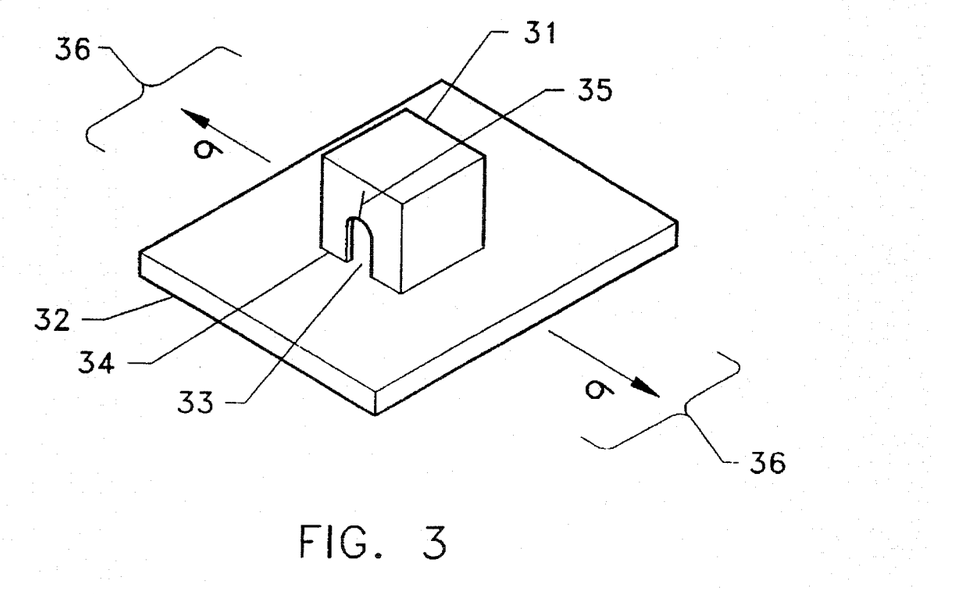
FIG. 3 is a perspective view of an alternate embodiment of the passive fatigue monitor.

Referring now to FIG. 3, an alternate embodiment 31 of the passive fatigue monitor is depicted bonded with adhesive 34 to a structural surface 32. A notch 33 with a precrack 35 is located at the apex of the notch on the alternate embodiment 31 with the device aligned with the principal direction of stresses as shown by $\sigma(36)$. The passive fatigue monitor may be configured in different shapes and sizes to suit specific needs without interfering with the operation of the device. The desired design criteria are as summarized above.

Figure 4:
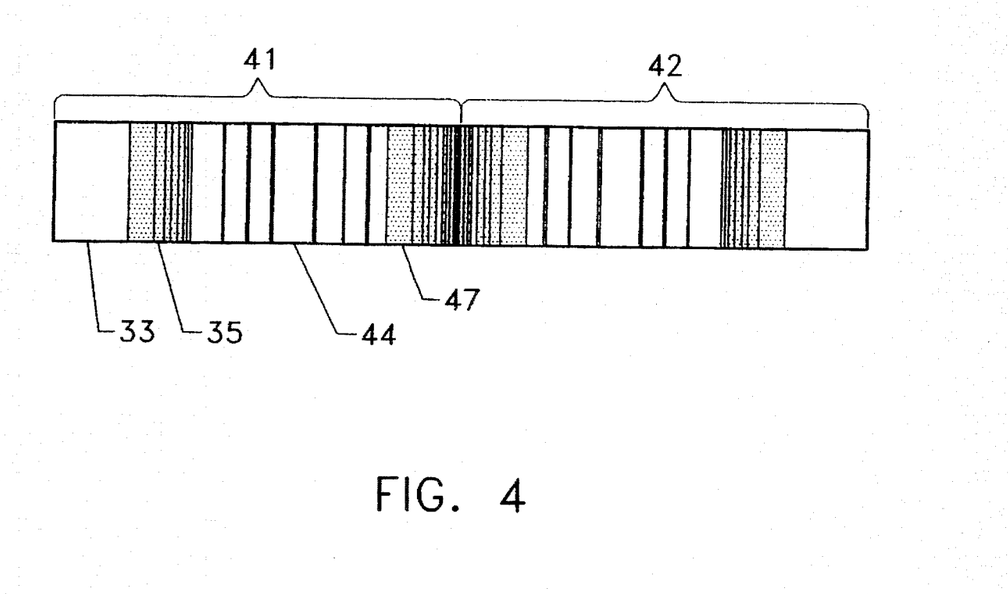
FIG. 4 is a view of the inside edge of the passive fatigue monitor after separating the right and left halves.

After applying a load cycle or cycles to the passive fatigue monitor, the monitor is removed from the surface and split apart along the precrack location. Referring now to FIG. 4, the left 41 and right halves 42 are shown after splitting of the passive fatigue monitor. Beginning on the left side of the drawing, the various regions are shown, the notch 33, the precrack 35 followed by the striations 44 and the fracture region 47. The striations 44 are the data containing structure, each peak and valley representing a single cycle of loading. As the striations are micro-structure, it may sometimes be necessary to provide contrast enhancement prior to analysis of the striations.

Unlike other patented methods, the proposed monitor directly and quantitatively measures load cycles and does so continuously, without power. When a stress cycle is experienced in the structure, a striation is micro-mechanically formed in the passive fatigue monitor. The number of striations recorded is independent of stress amplitude and is also independent of the geometry and composition of the structural member. The passive fatigue monitor may be placed on the structure at any time during service with state of fatigue being reconstructed. It is not necessary that the passive fatigue monitor and structure be the same material or that duplicate coatings be applied.

Figure 5A:
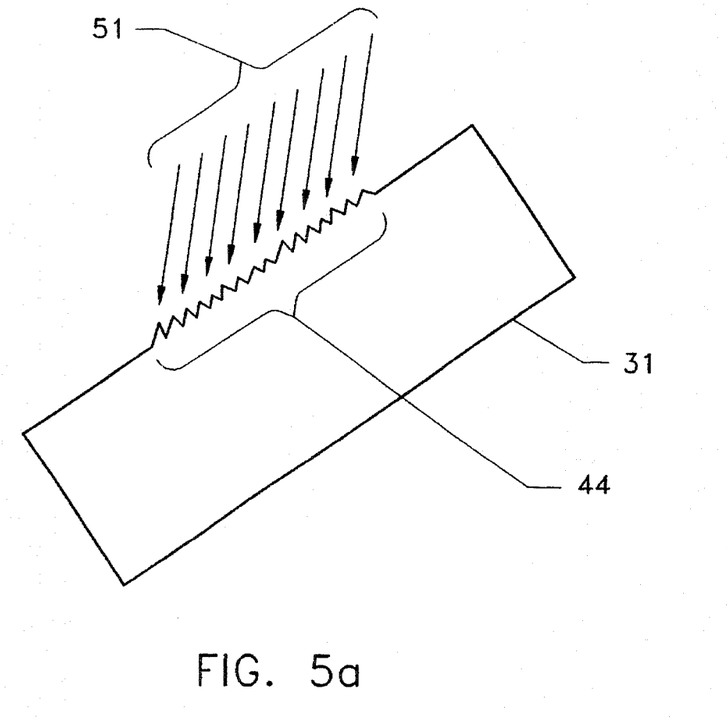
FIG. 5a is a partial side view of half of the passive fatigue monitor showing striations enhancement.
Figure 5B:
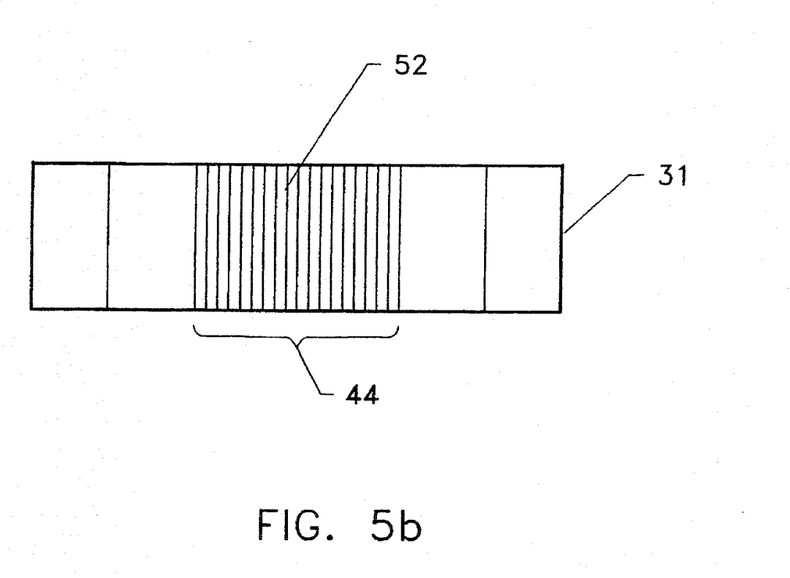
FIG. 5b is a top view of the same passive fatigue section as in the preceding figure.

Referring now to FIG. 5a, an edgewise view of the passive fatigue monitor 31 is shown at an exaggerated scale to show striations 44. The peaks and valleys of striation 44 are microstructural in nature and can be contrast-enhanced by adding carbon 51 to the surface. In the preferred embodiment, carbon vapor is used to form deposits. FIG. 5b depicts a top view of the passive fatigue monitor 31, showing striations 44 with carbon deposits 52 (after the adding of carbon 51 to the surface).

Figure 6:
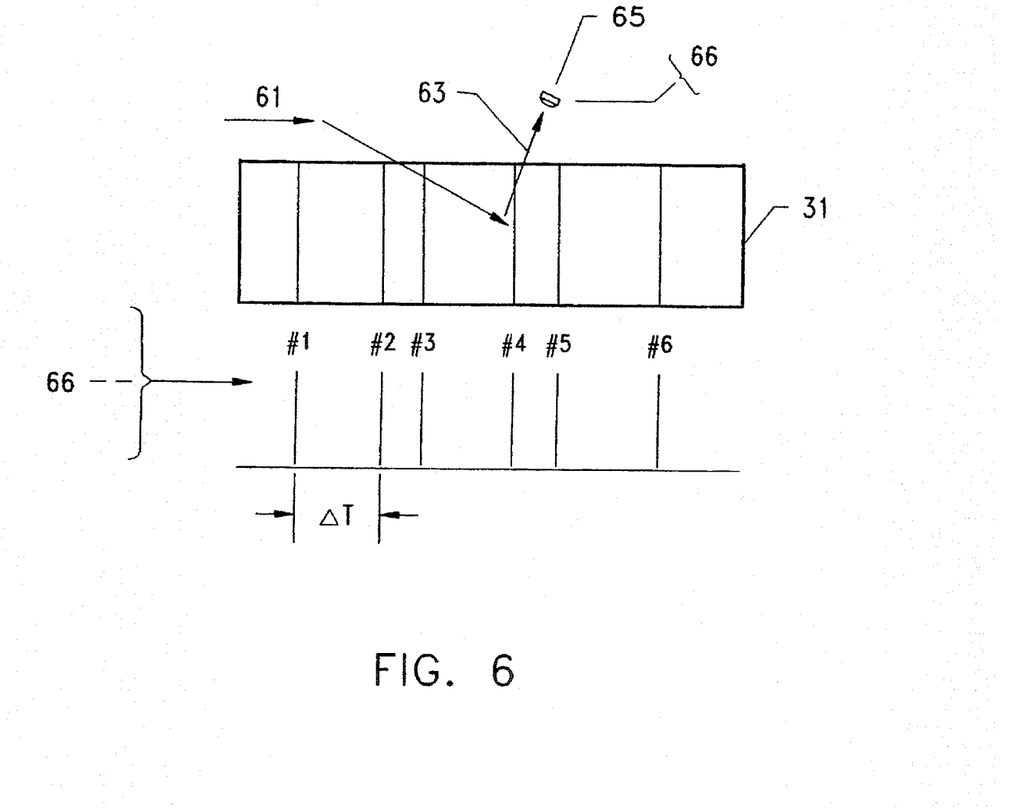
FIG. 6 is a schematic depicting the scanning of the enhanced striations.

After contrast enhancement of the striations, scanning of the surface of passive fatigue monitor 31 is accomplished as shown in FIG. 6. Preferably, a moving laser source 61 is used to illuminate spacing between dark stripes and the reflected energy 63 is captured by detector 65. Detector 65 produces an output 66 which is a voltage pulse train with voltage pulses (#1, #2, #3, #4, #5, #6) which occur over time intervals as depicted by $\Delta T$. It is also possible to accomplish conventional optical scanning without the use of a laser source by magnifying the striation region. Whichever technique is used, the time intervals, $\Delta T$, are converted to striation spacing based on a constant scan velocity V according to the relationship $$V = \Delta X / \Delta T$$

and thereafter converted to stress intensity ranges given by $$\text{Striation Spacing} = 6(\Delta K/E)^2$$

Figure 7:
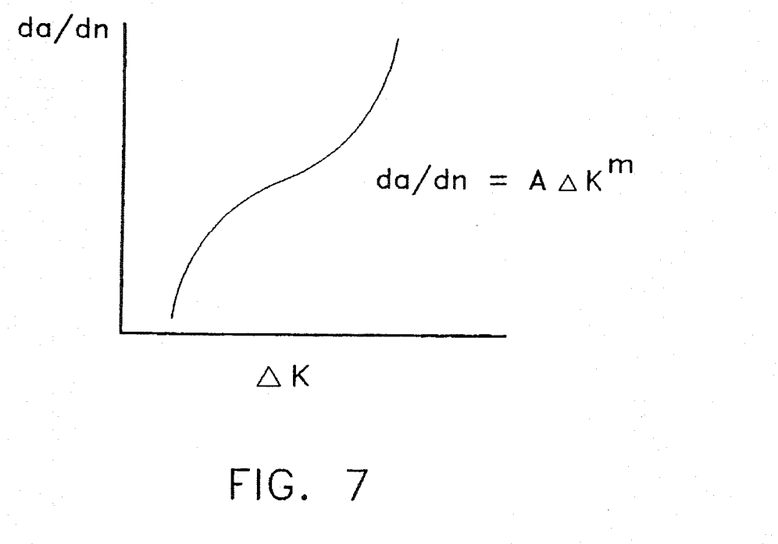
FIG. 7 is a plot of crack growth rate against stress intensity ranges.
Figure 8:
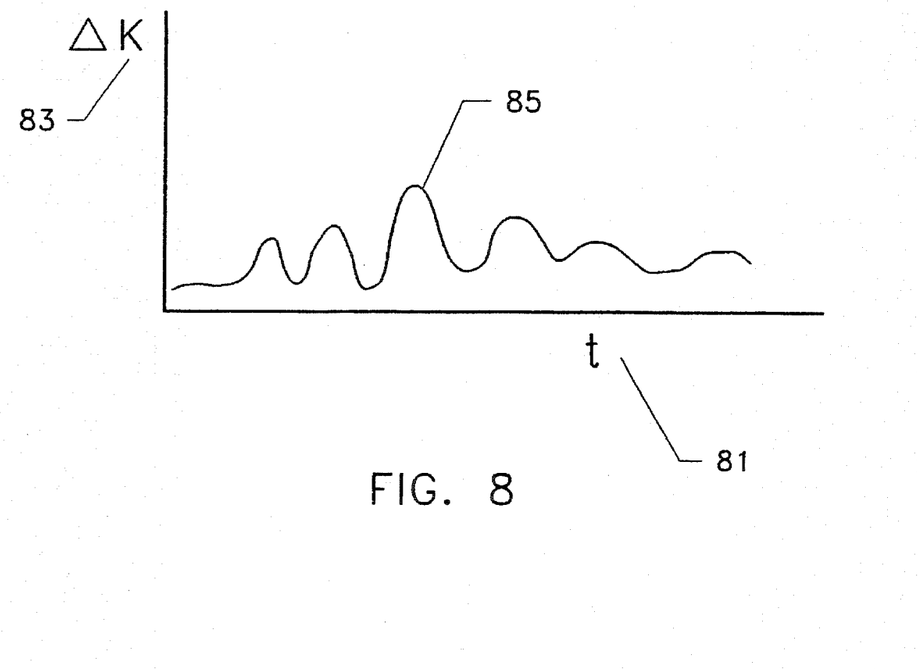
FIG. 8 is a plot of stress range against time.

Crack growth rate may now be plotted as depicted in FIG. 7 where the rate of change in the precrack length with respect to lead cycles (da/dn) is plotted against the stress intensity range ($\Delta K$). Likewise, referring to FIG. 8, $\Delta K$ can be correlated to time 81 or pulse voltage to provide a plot of stress range 83 versus time for a loading history 85. Finally, using the relationship (Miner's Rule) given by $$S_{re} = (\Sigma i \; \gamma_i S_{ri} 3)^{1/3}$$

a stress range histogram which plots percent frequency of ($\gamma_i$) of occurrence of stress cycles within stress ranges of finite magnitude intervals ($S_{ri}$) is used to calculate an equivalent constant amplitude stress range ($S_{re}$). This computation is analogous to determining root-mean-cube striation spacing by calculating the fraction of total fatigue cycles within discrete intervals of peak-to-peak distance. The striation data, which represents transferred strain from the structure, may be converted to stress values using the modules of elasticity of the striation-based fatigue monitor, thereby establishing a value for $S_{re}$.

Figure 9:
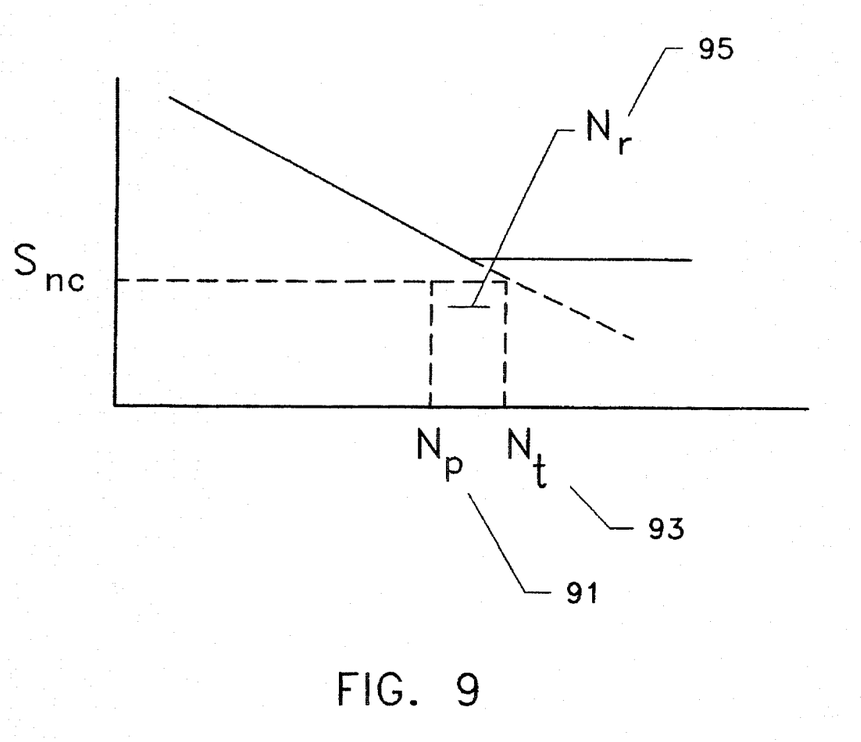
FIG. 9 is a graphical depiction of the cycles to failure plot which provides an estimate of remaining life.

The present number of fatigue cycles $N_p$, is equal to the cumulative number of striations provided that the passive fatigue monitor 91 is installed at or near the beginning of service life. As illustrated in FIG. 9, the remaining fatigue life, $N_r$ 95 may be estimated after determining the total fatigue life 93, $N_t$ at $S_{re}$, and calculating the difference $$N_r = N_t - N_p$$

Figure 10:
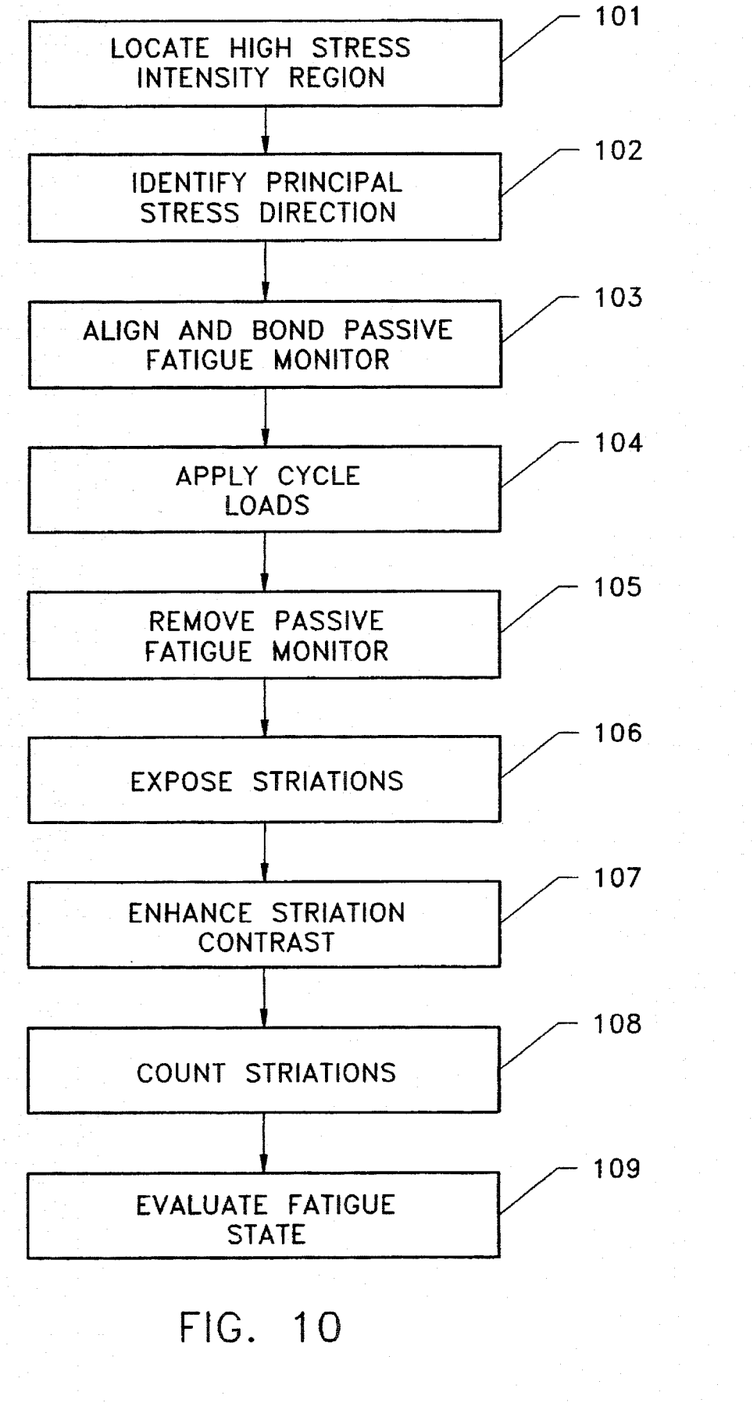
FIG. 10 is a flow chart depicting the steps which comprise the method of determining fatigue life.

The entire method is summarized as a series of steps in FIG. 10. After obtaining a material or structure to be evaluated, the first step 101 is to locate all regions of high stress intensities, typically by visual inspection to locate weld locations, surface interfaces, bends, notches, keyholes, or other surface discontinuities. The second step 102 is to identify the principal directions of stresses. This identification is accomplished by applying a photoelastic coating to the surface, illuminating the surface, and observing fringe patterns. The third step 103 is to align and bind the passive fatigue monitor with the precrack perpendicular to the direction of stress. The fourth step 104 is to apply cycles of loads to the structure with the bonded fatigue monitor in place. Step five 105 is to remove the fatigue monitor and in step six 106 separate the monitor along the line of the precrack so that the striation surface is exposed. Step seven 107 is to enhance the contrast of striations and, in step eight 108 count the striations using suitable optics or laser counters. The final step 109 is to evaluate the striation data to establish a time history and to further provide a projection of remaining life in the structural material.

The features and advantages of the invention are numerous. The striation monitor is not based on visual crack growth monitoring or any physical property monitoring such as acoustic signal generation, magnetic flux deviation, or changes in resistivity. The invention is instead based on microscopic development of fatigue striations which has been in the conceptual stage throughout the metallurgical community for over thirty years. (The striation technology, however, has never been applied to an extrinsic fatigue monitor.) As a result, the coupon of the present invention may be placed in service at any stage in the life cycle of the monitored structure and the coupon may be of any suitable material. There is no need to match the coupon material with that of the monitored structure. The striation monitor may be used at many locations of a structure to fully characterize its loading and fatigue behavior.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. A method for monitoring fatigue in a structure comprising the steps of:

providing passive fatigue monitors;

locating a region of high stress intensity on a structure;

identifying the principal direction of stresses on said structure;

aligning and bonding said passive fatigue monitors to said structure along the axes of principal stresses;

applying a cycle lead to generate stresses in said structure;

removing said passive fatigue monitor from said structure after the development of striation patterns independent of any crack formation or lack of formation;

determining the number of fatigue-induced striations; and evaluating the state of fatigue from the number of striations produced during the load application cycle.

2. A method for monitoring fatigue as in claim 1 wherein said step of locating a region of high stress intensity further comprises the locating the welds, surface interfaces, notches, keyholes and other surface discontinuities.

3. A method for monitoring fatigue in a structure comprising the steps of:

providing passive fatigue monitors;

locating a region of high stress intensity on a structure;

identifying the direction of principal stresses by applying a coating of photoelastic material to the structure and illuminating said structure to produce fringe patterns;

aligning and bonding said passive fatigue monitors to said structure along the axes of principal stresses;

applying a cycle load to generate stresses in said structure;

removing said passive fatigue monitor from said structure after the development of striation patterns independent of any crack formation or lack of formation;

determining the number of fatigue-induced striations; and evaluating the state of fatigue from the number of striations produced during the load application cycle.

4. A method for monitoring fatigue as in claim 3 wherein said step of determining the number of fatigue-induced striations further comprises:

exposing the striations formed on said passive fatigue monitors;

enhancing striation contrast; and counting the number of striations.

5. A method for monitoring fatigue as in claim 3 wherein said step of evaluating the state of fatigue further comprises assessing fatigue damage under variable applied stress range and then normalizing the assessed data to provide an equivalent constant amplitude stress range.

6. A method for monitoring fatigue as in claim 5 wherein said step of normalizing the assessed data comprises plotting a stress range histogram depicting the percent frequency of stress cycles within stress ranges of finite magnitude intervals.

7. A method for monitoring fatigue as in claim 3 wherein said step of providing a passive fatigue monitor further comprises providing a metal fatigue monitor having a face-centered cubic crystal structure.

8. A method for monitoring fatigue as in claim 7 wherein said step of providing a face-centered cubic crystal structure monitor comprises providing a fatigue monitor fabricated from a metal selected from the group of metals comprising aluminum, copper and nickel.

9. A method for monitoring fatigue as in claim 3 wherein said step of providing a passive fatigue monitor further comprises providing a ceramic fatigue monitor.

10. A method for monitoring fatigue as in claim 3 wherein said step of providing a passive fatigue monitor further comprises providing a polymer-based fatigue monitor.

11. A method for monitoring fatigue as in claim 3 wherein said step of providing a passive fatigue monitor further comprises providing a rubber-based fatigue monitor.

12. A method for monitoring fatigue as in claim 7 wherein said metal fatigue monitor is machined to provide a thinned plastic region and has a precrack cut transversely across the plastic region.

13. A method for monitoring fatigue as in claim 7 wherein said metal fatigue monitor has a notch machined in the undersurface of monitor and has a precrack cut into the apex of the notch.

14. A passive miniature fatigue monitor for producing striations independent of any crack formation or lack of formation comprising a coupon having bonding surfaces on a first end and on a second end and further having a reduced thickness center section, the center section having a precrack formed therein, the entire coupon being fabricated of a material that develops well-defined striations.

15. A passive miniature fatigue monitor as in claim 14 wherein said coupon is fabricated using a metal having a face-centered cubic crystal structure.

16. A passive miniature fatigue monitor as in claim 15 wherein said metal is selected from the group of metals comprising aluminum, copper and nickel.

17. A passive miniature fatigue monitor for producing striations comprising a coupon having bonding surfaces on a first end and on a second end and further having a reduced thickness center section, the center section producing fatigue induced striations independent of crack formations therein, the entire coupon being fabricated of a polymer-based material.

18. A passive miniature fatigue monitor as in claim 17 wherein said material is a rubber-based material.

* * * * *